United States Patent [19]

Chang et al.

[11] Patent Number: 5,252,613
[45] Date of Patent: Oct. 12, 1993

[54] ENHANCED CATALYST MIXING IN SLURRY BUBBLE COLUMNS (OP-3723)

[75] Inventors: Min Chang, Warren; Constantine A. Coulaloglou, Mendham, both of N.J.

[73] Assignee: Exxon Research & Engineering Company, Florham Park, N.J.

[21] Appl. No.: 992,983

[22] Filed: Dec. 18, 1992

[51] Int. Cl.$^5$ .............................. C07C 1/04
[52] U.S. Cl. .................................. 518/700
[58] Field of Search ........................ 518/700

[56] References Cited

U.S. PATENT DOCUMENTS

| | | | |
|---|---|---|---|
| 2,853,369 | 9/1958 | Kolbel et al. | 23/288 |
| 2,868,627 | 1/1959 | Kolbel et al. | 23/288 |
| 4,751,057 | 6/1988 | Westerman | 422/197 |

OTHER PUBLICATIONS

"Effects of Fine Bubbles on Flow Patterns in Bubble Column with Suspended Solid Particles" Morooka, et al., J. Chem Eng. of Japan, vol. 19, No. 6, 1986, pp. 507–512.

"Gas Holdup and Volumetric Liquid-Phase Mass Transfer Coefficient in Solid Suspended Bubble Column with Draught Tube", Koide, et al., J. Chem. Eng. of Japan, vol. 18, No. 3, 1985, pp. 248–254.

"Application of Airlift Gas-Liquid-Solid Reactors in Biotechnology", Siegel and Robinson, Chem Eng. Science vol. 47, No. 13/14, pp. 3215–3229, 1992.

"The Catalytic Synthesis of Hydrocarbons from $H_2/CO$ Mixtures over the Group VIII Metals", Vannice, J of Catalysis 37, 449–461, (1975).

"Hydrocarbon Synthesis, Hydrogenation and Cyclization" Emmett, Catalysis, vol. IV, pp. 103–108, Reinhold Publishing Corp. 1956.

"Titania-Supported Metals as CO Hydrogenation Catalysts", Vannice, Journal of Catalysis 74, 199–202 (1982).

"Sparged Loop Reactors" Joshi et al., The Canadian Journal of Chemical Engineering, vol. 68, Oct. 1990, 705–741.

"Reaction Technology in Bubble Columns" Deckwer, Fundamentals of Chemical Technology Process Technology of the Chemical and Related Industries, Otto Salle Verlag Publishers, Sauerlander Publishing 1985, Chapter 1.

"Loop Reactors" Blenke, Adv. Biochem Eng. vol. 13, 1979, pp. 121–214.

*Primary Examiner*—Howard T. Mars
*Attorney, Agent, or Firm*—Joseph J. Allocca

[57] ABSTRACT

Catalyst particle distribution and mixing in slurry part of bubble columns is improved by introducing a secondary suspending fluid into the columns at locations within the lower 20% of the vertical height of the column but above the gas distributor normally located at or near the bottom of the columns.

5 Claims, 2 Drawing Sheets

ENHANCED CATALYST MIXING IN SLURRY BUBBLE COLUMNS (OP-3723)

FIELD OF THE INVENTION

The present invention is a method and means for improving catalyst particle distribution and mixing in slurry bubble columns, the catalyst being primarily distributed and suspended in the slurry by the energy imparted from the synthesis gas rising from the gas distribution means at the bottom of the slurry bubble column, said improved catalyst distribution and mixing being obtained by introducing a secondary stream of gas into the slurry bubble column by use of secondary gas introduction means located within the column at a location above the gas distribution means at the bottom of the slurry bubble column.

The secondary gas stream may comprise a portion of the reactive feed gas or recycle gas or it may be separately added inert gas, or condensed light hydrocarbons or process end products which vaporize under the conditions present at the location of introduction.

BACKGROUND OF THE INVENTION

Slurry reactors are well known for carrying out highly exothermic, three phase, catalytic reactions. Usually called "slurry bubble columns" these reactors have a liquid phase in which solid catalyst particles are dispersed or held in suspension by a gas phase bubbling through the liquid phase, thereby creating a slurry. These reactors provide improved heat transfer characteristics for the exothermic reaction, and the bubbling gas provides essentially all of the energy necessary for maintaining the catalyst dispersed in the liquid phase.

Bubble column reactors typically have a multiplicity of tubes suspended within a shell-type housing, the tubes being filed with a heat transfer medium, e.g., steam, which absorbs the heat generated by the exothermic reaction occurring on the shell side of the tubes in the main body of the housing.

Alternatively the reactor can be of a similar multitube design housed in a common shell-type housing as previously described but wherein the gas and liquid are passed through the multiple tubes which function as the reactor tubes, with effluent being removed from the upper ends of the reactor tubes and heat transfer fluid is passed through the space along the outside surfaces of the reactor tubes. The reactor tubes can be either multiple individual tubes with spaces between adjacent tubes, or multiple bundles of tubes with spaces between adjacent bundles of tubes.

Likewise the entire cross section of the reactor vessel may have a plurality of shafts disposed within it, the bottoms of said shafts being located above the reaction gas inlet but extending a distance above the top surface of the reaction slurry into the gas disengaging spaces so as to create multiple single columns of standing, non-circulating liquid with catalyst suspended and dispersed in said standing liquid. The reaction zone therefor has multiple single columns, said columns having a common bottom reaction gas introduction zone and a common upper gas disengagement space. To insure proper control of the exothermic process additional tubes can be inserted into or between the multiple single columns to function as heat exchangers.

As previously stated, in slurry bubble columns, the catalyst particles are suspended by the gas entering the bubble columns through bottom sited distributors. Often, catalyst particles in these reactors are non-uniformly distributed in the axial direction of the reactor vessel within the range of gas velocities of interest to the practitioner. Under these conditions the reactor operation is limited by "hot spots" which are formed by zones of catalyst near the bottom of the column where the highest catalyst concentration is found or in stagnant eddy current circulating zones. Non-uniform catalyst distribution also contributes to non-uniform catalyst aging and inefficient catalyst utilization insofar as the reaction progresses only when reactants are in contact with catalyst. In hydrocarbon synthesis processes such "hot spots" force the reactor to operate under less than maximum efficiency conditions.

It would be an advance if, in whatever configuration the reaction vessel may take, catalyst within the slurry reaction vessel could be more uniformly distributed and circulated so as to insure more even catalyst aging in the course of the reaction, more effective use of the catalyst by insuring a higher probability that the maximum amount of available catalyst is circulating in the reaction zone to promote the reaction by eliminating stagnant zones of standing catalyst.

SUMMARY OF THE INVENTION

Figure 1:
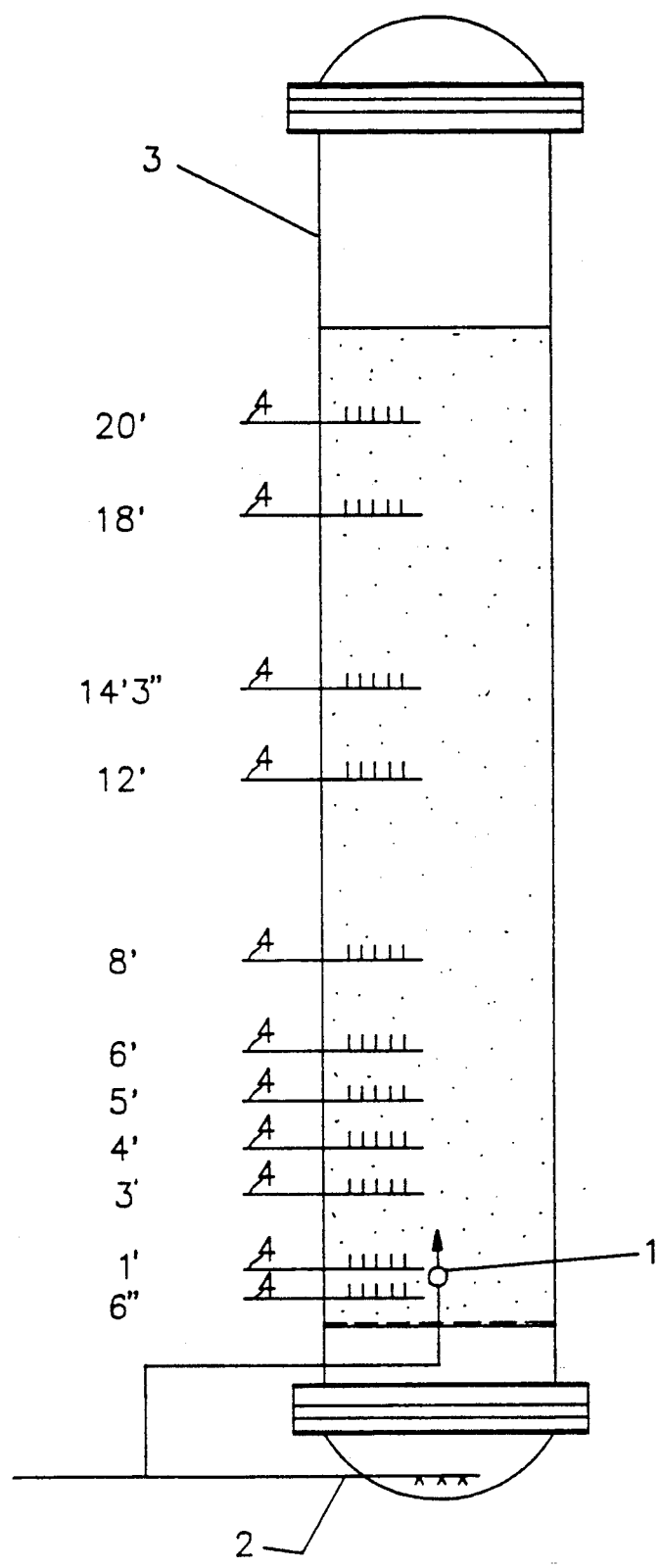
FIG. 1 presents a schematic of the apparatus used to demonstrate the benefit of using secondary gas injection on solids distribution in a slurry reactor.

Improved catalyst circulation, distribution and utilization are secured in slurry bubble columns, which use rising gas introduced from gas distribution means located at the bottom of said columns to provide the majority of the energy involved in dispersing catalyst in said slurry bubble columns, by using a secondary fluid introduction means in said slurry bubble column at a location above the gas distribution means located at the bottom of said column to introduce a secondary fluid stream into said column. The secondary fluid takes the form of a gas or mixture of gas and liquid and may comprise part of the synthesis feed gas or recycle gas or a secondary non-reactive gas stream such as inert gas alone or in combination with a liquid such as condensed light hydrocarbons or light synthesis hydrocarbons. The secondary fluid can also take the form of condensed light hydrocarbons or light synthesis hydrocarbons which totally or partially vaporize under the conditions present in said columns at the locations of introduction.

The secondary fluid introduction means, located above the synthesis gas introduction means sited at the bottom of the slurry bubble column, may take any convenient form including single and multiple-individual injection venturi or nozzles. Each nozzle or venturi can be fed by its own dedicated source of secondary fluid or, in the case of multiple-individual nozzles fitted into the slurry bubble columns, they may be serviced by a common manifold. In another alternative a configuration of pipe fitted with either a single or multiple secondary fluid service lines can be equipped with multiple nozzles or venturi, the configuration of pipe being sited at a distance above the synthesis gas introduction means which is located at the bottom of the slurry bubble column. The configuration of pipe can take the form of a circle, triangle, square, L, star burst (with arms radiating from a common center), spoked wheel, etc.

When multiple nozzles are employed the flow through each nozzle can be balanced and adjusted to achieve even flow out of each nozzle. This, however, is not critical to the present invention, and unbalanced flow through multiple nozzles fed by single or multiple feed lines is acceptable.

As previously stated, the secondary fluid introduction means are sited above the synthesis gas introduction means which are located at the bottom of the slurry bubble column. The exact distance of the secondary gas introduction means above the synthesis gas introduction means is not critical but it is preferred that placement be above and not in the same horizontal plane as the synthesis fluid introduction means. It is preferred that the secondary gas introduction means be sited within the lower 20% of the vertical height of the column but preferably above the main synthesis gas introduction means.

Volume of flow through the secondary fluid introduction means depends on the nature of the secondary fluid employed.

If the material used in the secondary fluid introduction means is synthesis gas, recycle gas, or inert gas, because the total gas introduced by both the primary and secondary gas introduction means must fall within the operable gas handling limits, of the synthesis reactor this total is split between the two introduction means. In general, the total gas rate fed to the reactor ranges from a minimum of about 2 cm/sec up to the design limit of the reactor, with the split between primary and secondary introduction ranging from, about 30/70 to 70/30, preferably about 50/50 to 70/30.

When the secondary fluid comprises gas plus liquid, the liquid component of the combination comprises about 1 to 5 wt% of the secondary fluid.

As stated, the present invention is of use in slurry bubble columns used for hydrocarbon synthesis processes wherein gas, i.e., hydrogen and carbon monoxide, in a ratio ranging from about 0.5 to 4, preferably 0.7 to 2.75, more preferably about 0.7 to 2.5, or other synthesis feed such as methanol, is injected into a reactor at superficial gas velocities ranging from about 1 to 30 cm/sec through the gas injection means such as bubble caps, spargers or multi-cone arrays into the main reaction zone in which is located hydrocarbon synthesis product (i.e. hydrocarbon liquids or liquid wax) and catalyst. The gases bubble up through the reaction zone in contact with the catalyst in the hydrocarbon liquid and are converted into hydrocarbon product.

Reaction takes place wherever there are synthesis gas, catalyst and suitable reaction conditions, which include pressures ranging from 1 to 100 atmospheres, preferably 10 to 50 atmospheres, more preferably about 15 to 40 atmospheres and temperatures ranging from about 175° C. to about 450° C., preferably about 175° C. to 420° C., more preferably about 175° C. to 300° C.

The slurry phase liquids in which the catalyst is dispersed are those that are liquid at reaction conditions, generally inert, and a good solvent for synthesis gas. Typically, the slurry is the product of the reaction and contains $C_5+$ hydrocarbons, usually $C_5-C_{100}$ hydrocarbons. Preferably, however, the slurry liquid comprises primarily high boiling paraffins with small amounts of primary and secondary alcohols, acids, esters, or mixtures thereof. Sulfur, nitrogen, phosphorus, arsenic, or antimony heteroatoms are to be avoided since these tend to poison the hydrocarbon synthesis catalyst. Examples of specific slurry liquids are dodecane, tetradecane, hexadecane, octadecane, tetracosane, and the like. Preferred slurry materials are Fischer-Tropsch waxes and $C_{16}-C_{18}$ hydrocarbons.

The concentration of solids, including catalyst, in the slurry phase is usually about 5–60% by weight, preferably 10–50 wt % solids.

The hydrocarbon synthesis reaction is highly exothermic and the heat of reaction is removed by a heat transfer material which is either circulating on the shell side of a shell and the tube reactor when the reaction takes place in the tube, or through the tubes when the reaction takes place on the shell side. The common heat transfer material can be any material having a high heat capacity, whether or not it undergoes a phase change. Preferably the heat transfer fluid is boiling water.

The catalyst employed in the hydrocarbon synthesis process is any catalyst known to be active in Fischer-Tropsch synthesis. For example, Group VIII metals, whether supported or unsupported, are known Fischer-Tropsch catalysts. Of these, iron, cobalt and ruthenium are preferred, particularly iron and cobalt, most particularly cobalt.

A preferred catalyst is supported on an inorganic refractory oxide selected from Groups III, IV, V, VI, and VIII of the Periodic chart of the elements. Preferred supports include silica, alumina, silica-alumina, the Group IVB oxides, most preferably titania (primarily in the rutile form), and generally supports having a surface area of less than about 100 $m^2/gm$, preferably 70 $m^2/gm$ and less.

The catalytic metal is present in catalytically active amounts, usually about 1–100 wt % the upper limit being attained in the case of iron based catalysts, preferably 2–40 wt %, more preferably about 2–25 wt %. Promoters may be added to the catalyst and are well known in the Fischer-Tropsch catalyst art. Promoters can include ruthenium (when it is not the primary catalytic metal), rhenium, hafnium, cerium, and zirconium, and are usually present in amounts less than the primary catalytic metal (except for ruthenium which may be present in coequal amounts), but the promoter:metal ratio should be at least about 1:10. Preferred promoters are rhenium and hafnium.

Catalyst preparation may be accomplished by a variety of techniques, although catalyst preparation does not play a part in this invention.

A typical catalyst preparation may involve impregnation, by incipient wetness or other known techniques of, e.g., a cobalt nitrate salt onto a titania, silica, or alumina support, optionally followed or proceeded by impregnation with a promoter material, e.g., perrhenic acid. Excess liquid is removed and the catalyst precursor dried at 100° C. to 125° C. Following drying or as a continuation thereof, the catalyst is calcined at about 300°-C.-500° C. to convert the salt or compound to its corresponding oxide(s). The oxide is then reduced by treatment with hydrogen or a hydrogen containing gas at about 300°-C.-500° C. for a period of time sufficient to substantially reduce the oxide to the elemental or catalytic form of the metal. Some prefer an additional cycle of oxidation/reduction. Another, and sometimes preferred method for catalyst preparation is disclosed in U.S. Pat. No. 4,621,072 incorporated herein by reference.

Catalyst particle size is not critical and particle sizes may range from that which is reasonably filterable to that which is reasonably able to be dispersed in a slurry phase. Particle sizes of 1-200 microns, preferably about 20 to 150 microns meet these requirements.

EXAMPLES

Two experiments were carried out by injecting part of the feed gas through a centrally located secondary gas introduction nozzle (1) located one foot above the primary gas introduction means (2) in a 5 foot diameter by 30 foot high slurry bubble column (3) fitted with radial sample probes (4) (FIG. 1). Catalyst dispersion (mixing) data are compared at total gas superficial velocities which are held constant within each example (although differing between the examples).

Figure 2:
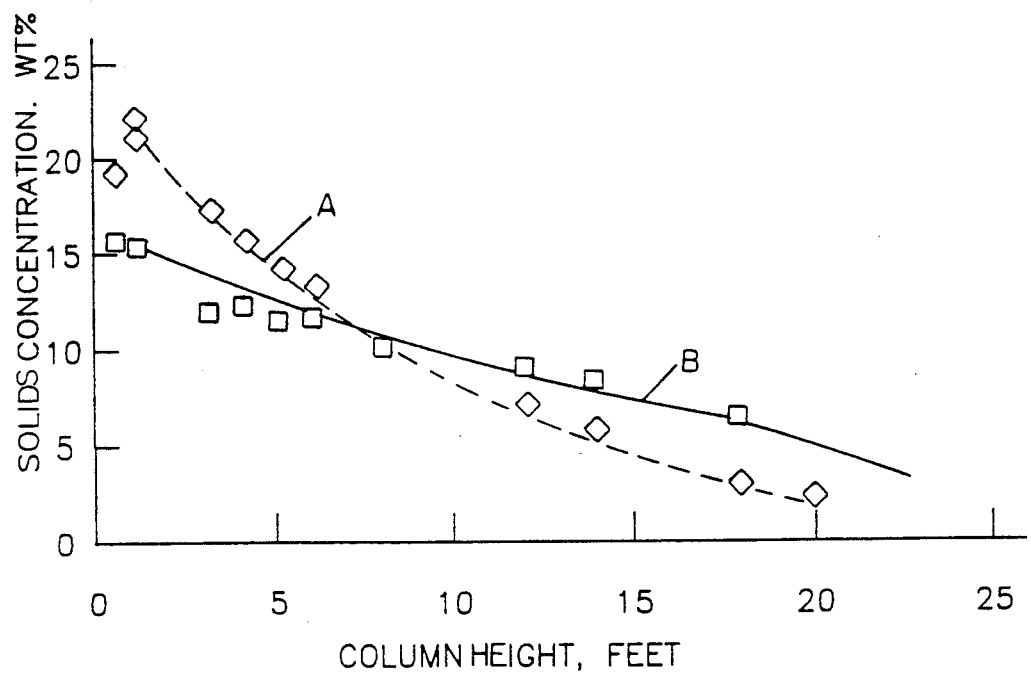
FIG. 2 presents a comparison of catalyst solids distributor achieved at a superficial gas velocity of 7.4 cm/sec when the gas is introduced solely through the synthesis gas introduction means and when the same total amount of gas at the same total superficial gas velocity is divided between synthesis gas introduction means and secondary gas introduction means.

In FIG. 2 the total gas superficial velocity was 7.4 cm/sec. When this was introduced solely through the main gas distribution means catalyst distribution according to curve A was secured. When this was split between primary and secondary gas distribution means at a ratio of 5/2.4 catalyst distribution according to curve B was secured.

Figure 3:
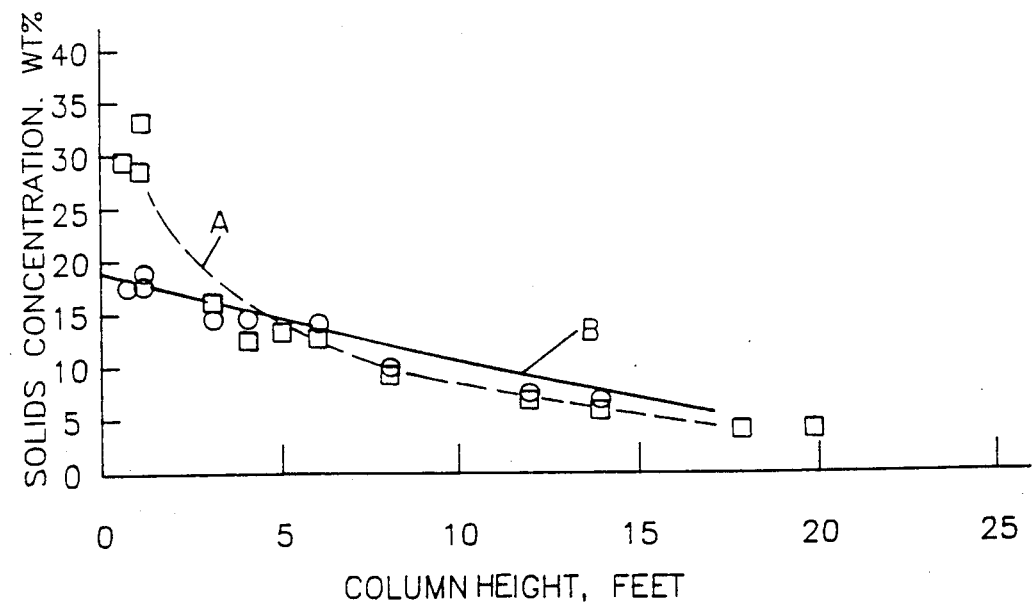
FIG. 3 is the same experiment as FIG. 2 but the total superficial gas velocity is 4 cm/sec.

In FIG. 3 total gas superficial velocity was 4 cm/sec. Again when this total was introduced solely through the main gas distribution means, catalyst distribution according to curve A was secured while when this was split between primary and secondary gas distribution means then secondary gas distribution means being at a height of 1 foot above the primary gas distribution means and at a 2/2 ratio catalyst distribution according to curve B was secured.

For both cases improvement in axial catalyst distribution was observed (FIGS. 2 and 3). The gas introduced into the slurry bubble column was nitrogen through both the primary and secondary gas distribution means insofar that these runs measured only catalyst distribution in the column and were not synthesis runs.

What is claimed is:

1. A method for improving the axial distribution of catalyst in a hydrocarbon synthesis slurry bubble column which uses rising synthesis gas introduced by means of synthesis gas distribution means located at the bottom of said column to provide the majority of the energy used in distributing catalyst in said column, the improvement in axial distribution of catalyst being achieved by using a secondary fluid introduction means in said slurry bubble column at a location above the synthesis gas distribution means located at the bottom of said column to introduce a secondary fluid stream into said column.

2. The method of claim 1 wherein the secondary fluid stream comprises part of the synthesis gas feed, recycle gas, non-reactive/inert gas, condensed light hydrocarbons or light synthesis hydrocarbons which vaporize under the conditions present in said column at the point of introduction and mixtures thereof, and mixtures of said gases with condensed light hydrocarbon or light synthesis hydrocarbon liquids.

3. The method of claim 1 wherein the secondary fluid introduction means is located within the lower 20% of the vertical height of the column above the synthesis gas introduction means.

4. The method of claim 1 wherein when the secondary fluid introduced by the secondary fluid introduction means is a gas, the split in gas rate between the synthesis gas introduction means and the secondary gas introduction means ranges from 30:70 to 70:30.

5. The method of claim 4 wherein when the secondary fluid introduced by the secondary fluid introduction means is a mixture of gas and liquid the rate of liquid introduction into the column through said secondary fluid introduction means is about 1 to 5 wt % of the secondary fluid introduction rate.

* * * * *